United States Patent
Wilson et al.

(10) Patent No.: US 7,272,508 B2
(45) Date of Patent: *Sep. 18, 2007

(54) SMALL MOLECULE MIMETICS OF ERYTHROPOIETIN

(75) Inventors: Ian A. Wilson, La Jolla, CA (US); Oded Livnah, San Diego, CA (US); Enrico A. Stura, San Diego, CA (US); Dana L. Johnson, Upper Black Eddy, PA (US); Linda K. Jolliffe, Belle Mead, NJ (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/252,390

(22) Filed: Oct. 17, 2005

(65) Prior Publication Data

US 2006/0064252 A1    Mar. 23, 2006

Related U.S. Application Data

(63) Continuation of application No. 10/985,720, filed on Nov. 10, 2004, now abandoned, which is a continuation of application No. 10/028,564, filed on Dec. 21, 2001, now abandoned, which is a continuation of application No. 09/189,745, filed on Nov. 10, 1998, now abandoned, which is a continuation of application No. 08/641,071, filed on Apr. 26, 1996, now Pat. No. 5,835,382.

(51) Int. Cl.
*G01N 33/48* (2006.01)
*G06F 7/00* (2006.01)

(52) U.S. Cl. ............ 702/20; 702/19; 702/27; 703/11; 703/12; 707/102; 435/7.1; 435/7.2

(58) Field of Classification Search .......... 702/19, 702/20, 27
See application file for complete search history.

(56) References Cited

U.S. PATENT DOCUMENTS

| | | | |
|---|---|---|---|
| 4,674,066 A | 6/1987 | Kucera | |
| 5,265,030 A | 11/1993 | Skolnick et al. | |
| 5,292,654 A | 3/1994 | Akihiko et al. | |
| 5,331,573 A | 7/1994 | Balaji et al. | |
| 5,434,796 A | 7/1995 | Weininger | |
| 5,436,850 A | 7/1995 | Bowie et al. | |
| 5,506,107 A | 4/1996 | Mulkerrin et al. | |
| 5,555,366 A | 9/1996 | Teig et al. | |
| 5,557,535 A | 9/1996 | Srinivasan et al. | |
| 5,835,382 A * | 11/1998 | Wilson et al. | 702/27 |

FOREIGN PATENT DOCUMENTS

| | | |
|---|---|---|
| EP | 0 612 846 | 8/1994 |
| WO | WO94/25055 | 11/1994 |
| WO | WO95/11487 | 4/1995 |
| WO | WO96/40772 | 12/1996 |

OTHER PUBLICATIONS

Livnah et al. "Functional Mimicry of a Protein Hormone by a Peptide Agonist: The EPO Receptor Complex at 2.8. A" Science 273:464-471, 1996.
McCarthy, M. "Small Peptide Designed that can Mimic Erythropoietin" The Lancet 348:395, 1996.

* cited by examiner

*Primary Examiner*—Mary K. Zeman
(74) *Attorney, Agent, or Firm*—Fish & Richardson P.C.

(57) ABSTRACT

The invention features computer-assisted methods for identifying molecules which will bind to the EPO receptor and act as an erythropoietin (EPO) mimetic. Preferred EPO mimetics identified using the method of the invention act as agonists of the EPO receptor in one or more in vitro or in vivo biological assays of EPO activity.

2 Claims, 2 Drawing Sheets

SMALL MOLECULE MIMETICS OF ERYTHROPOIETIN

RELATED APPLICATION INFORMATION

This application is a continuation of U.S. application Ser. No. 10/985,720, filed Nov. 10, 2004 now abandoned, which is a continuation of U.S. application Ser. No. 10/028,564, filed on Dec. 21, 2001 now abandoned, which is a continuation of U.S. application Ser. No. 09/189,745, filed Nov. 10, 1998 now abandoned, which is a continuation of U.S. application Ser. No. 08/641,071, filed Apr. 26, 1996 now U.S. Pat. No. 5,835,382, all of which are hereby incorporated by reference.

GOVERNMENT SUPPORT

This invention was made with U.S. Government support under the National Institutes of Health Grant Nos. GM49491 and GM38794. The U.S. Government has certain right in the invention.

BACKGROUND OF THE INVENTION

1. Field of the Invention

This invention relates to computer-assisted methods for identifying and designing small molecule mimetics of erythropoietin.

2. Description of Related Art

Erythropoietin (EPO) is the primary regulator of the proliferation and differentiation of immature erythroid cells. EPO is produced in the fetal liver and in the adult kidney in response to hypoxia (low oxygen levels in blood or tissue). It circulates in the blood stream where it targets the EPO receptor (EPOR) on committed progenitor cells in the bone marrow and other hematopoietic tissues. Recombinant human erythropoietin (rHuEPO) is widely used in therapy of patients with anaemia due to chronic renal failure, cancer chemotherapy and AZT treatment.

The EPO receptor belongs to the cytokine receptor superfamily which includes receptors for other hematopoietic growth factors such as interleukins (ELs), colony stimulating factors (CSFs) as well as growth hormone prolactin and ciliary neurotrophic factor (CNTF). The structural architecture of this family of receptors consists of three modules: a ligand binding extracellular domain, a short trans membrane region and a large cytoplasmic domain. It has been proposed that the extracellular domain of this superfamily comprises two discrete domains each containing approximately 100 residues that fold into a sandwich consisting of 7 antiparallel .beta.-strands with the topology of an Ig constant domain. Members of the family share two characteristic motifs in their extracellular domain: a pair of conserved disulfide bridges in the N-terminal domain, and a WSXWS box (SEQ ID NO:2) (where X is any amino acid residue) in the C-terminal domain. For most members of this receptor superfamily, oligomerization of one or more polypeptide chains is essential for forming high affinity receptor complexes. A homodimer complex has been demonstrated to be the active form of hGHR and a similar model has been suggested for G-CSF, prolactin and EPO receptors.

Erythropoietin induces dimerization of two EPO receptor molecules, which results in subsequent phosphorylation of the cytoplasmic domains by the association with two tyrosine kinase (JAK2) molecules to initiate a cascade of events that leads to the relevant biological.

Given the importance of erythropoietin, it would be very desirable to be able to identify molecules capable of binding the EPO receptor and eliciting the response normally elicited by EPO.

SUMMARY OF THE INVENTION

The invention features methods for identifying molecules which will bind to the EPO receptor and act as a EPO mimetic. Preferred EPO mimetics identified using the method of the invention act as agonists of the EPO receptor in one or more in vitro or in vivo biological assays of EPO activity. Preferred mimetics are molecules lacking peptide bonds, i.e., are non peptidic mimetics. Preferred peptide mimetics have 15 or fewer, more preferably 10 or fewer amino acids.

The methods of the invention entail identification and design of molecules having a particular structure. The methods rely on the use of precise structural information derived from x-ray crystallographic studies of the extracellular domain of EPO receptor (amino acids 1 to 225) complexed with a peptide, EMP1 (EPO Mimetic Peptide 1; described below), which acts as an EPO mimetic. This crystallographic data permits the identification of atoms in the peptide mimetic that are important for EPO receptor binding and dimerization. More importantly, this data defines a three dimensional array of the important contact atoms. Other molecules which include a portion in which the atoms have a similar three dimensional arrangement similar to some or all of these contact atoms are likely to be capable of acting as an EPO mimetic. Moreover, one can use the structural information to design or identify molecules having even more EPO activity than the peptide mimetic described herein.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

Like reference numbers and designations in the various drawings indicate like elements.

DETAILED DESCRIPTION OF THE INVENTION

Throughout this description, the preferred embodiment and examples shown should be considered as exemplars, rather than as limitations on the present invention.

Described below is the crystal structure of a small peptide mimetic of EPO bound to an extracellular portion of the EPO receptor. The peptide, EMP1 (GGTYSCHFG-PLTWVCKPQGG; SEQ ID NO:1), is characterized by an intramolecular disulfide bridge. Several lines of evidence suggest that EMP1 can act as an EPO mimetic. For example, EMP1 competes with EPO in receptor binding assays and induces cellular proliferation of cell lines engineered to be responsive to EPO. Both EPO and peptide induce a similar cascade of phosphorylation events and cell cycle progression in EPO responsive cells. Further, EMP1 demonstrates significant erythropoietic effects in mice as monitored by two different in vivo assays of nascent red blood cell production. This data, when combined, strongly supports the notion that the peptide ligand, which has a sequence unrelated to that of EPO, is capable of binding to and inducing an agonist conformation or assembly of EPO receptor.

Design of Small Molecule Mimetics

The structure of the EMP1 dimer demonstrates that a molecule substantially smaller than the natural hormone can act as an agonist and induce the appropriate biological response. The peptide is assumed to have a substantially smaller contact interface with the receptor than its natural hormone. The binding determinants in the EPO receptor form an almost flat surface which is mainly hydrophobic in nature, without any cavities or charged residues that may help in design of a small molecule ligand to interact with the receptor.

This simplified framework of interactions revealed by the structural data presented herein can be used to identify additional EPO mimetics. The atoms of EMP1 which are important for binding to the EPO receptor and forming dimeric EPO receptor include those involved in the contact between the EMP1 (peptide) and EBP (EPO receptor) and those involved in contacts between the two EMP1 molecules in the dimeric complex (peptide-peptide contacts). In addition to the contacts listed in Table 2, the following EMP1-EMP1 hydrophobic contacts are significant: $Tyr^{P4}$, $Cys^{P6}$, $Phe^{P8}$, $Trp^{P13}$, and $Cys^{P15}$ in each peptide. The following EMP1-EBP hydrophobic interactions are also significant: $Tyr^{P4}$, $Phe^{P8}$, and $Trp^{P13}$ in each peptide. It will be understood by those skilled in the art that not all of the atoms present in a significant contact residue need be present in a mimetic. In fact, it is only those few atoms which actually from important contacts with the EPO receptor which are likely to be important for mimetic activity. Those skilled in the art will be able to identify these important atoms based on the model of the dimeric EMP1-EPO complex which can be constructed using the structural data herein.

Preferred mimetics will include atoms at postions similar to those of the EPO receptor contacting atoms of EMP1. Even more preferred mimetics will be structurally similar to the dimer of EMP1 found in the structure described below. This is because the dimerization of EMP1 is an important factor in the diemerization of the EPO receptor.

The methods of the invention employ a computer-based methods for identifying compounds having a desired structure. More specifically, the invention uses the three-dimensional coordinates of a subset of the atoms in the peptide GGTYSCHFGPLTWVCKPQGG (SEQ ID NO:1) when the peptide is co-crystallized with a portion of the erythropoietin receptor comprising amino acids 1 to 225 of the human EPO receptor, to determine peptide and non-peptide mimetic candidates by means of computer methods.

These computer-based methods fall into two broad classes: database methods and de novo design methods. In database methods the compound of interest is compared to all compounds present in a database of chemical structures and compounds whose structure is in some way similar to the compound of interest are identified. The structures in the database are based on either experimental data, generated by NMR or x-ray crystallography, or modeled three-dimensional structures based on two-dimensional (i.e., sequence) data. In de novo design methods, models of compounds whose structure is in some way similar to the compound of interest are generated by a computer program using information derived from known structures, e.g., data generated by x-ray crystallography and/or theoretical rules. Such design methods can build a compound having a desired structure in either an atom-by-atom manner or by assembling stored small molecular fragments.

The success of both database and de novo methods in identifying compounds with activities similar to the compound of interest depends on the identification of the functionally relevant portion of the compound of interest. For drugs, the functionally relevant portion is referred to a pharmacophore. A pharmacophore then is an arrangement of structural features and functional groups important for biological activity, e.g., EPO activity.

Not all identified compounds having the desired pharmacophore will act as an EPO mimetic. The actual activity can be finally determined only by measuring the activity of is the compound in relevant biological assays. However, the methods of the invention are extremely valuable because they can be used to greatly reduce the number of compounds which must be tested to identify an actual mimetic.

Dimerization of the EPO receptor is important for activity. Accordingly, preferred mimetics will be based on the structure of the EMP1 dimer as it is bound to the EPO receptor dimer. Thus, preferred mimetics have include important contacts from both of the RWJ 61233 peptides present in the structure described below. Such mimetics will favor dimerization of the EPO receptor.

Programs suitable for generating predicted three-dimensional structures from two-dimensional data include: Concord (Tripos Associated, St. Louis, Mo.), 3-D Builder (Chemical Design Ltd., Oxford, U.K.), Catalyst (Bio-CAD Corp., Mountain View, Calif.), and Daylight (Abbott Laboratories, Abbott Park, Ill.).

Programs suitable for searching three-dimensional databases to identify molecules bearing a desired pharmacophore include: MACCS-3D and ISIS/3D (Molecular Design Ltd., San Leandro, Calif.), ChemDBS-3D (Chemical Design Ltd., Oxford, U.K.), and Sybyl/3DB Unity (Tripos Associates, St. Louis, Mo.).

Programs suitable for pharmacophore selection and design include: DISCO (Abbott Laboratories, Abbott Park, Ill.), Catalyst (Bio-CAD Corp., Mountain View, Calif.), and ChemDBS-3D (Chemical Design Ltd., Oxford, U.K.).

Databases of chemical structures are available from Cambridge Crystallographic Data Centre (Cambridge, U.K.) and Chemical Abstracts Service (Columbus, Ohio).

De novo design programs include Ludi (Biosym Technologies Inc., San Diego, Calif.) and Aladdin (Daylight Chemical Information Systems, Irvine Calif.).

Those skilled in the art will recognize that the design of a mimetic may require slight structural alteration or adjustment of a chemical structure designed or identified using the methods of the invention.

In general, chemical compounds identified or designed using the methods of the invention can be sythesized chemically and then tested for EPO activity using any of the methods described below. The methods of the invention are particularly useful because they can be used to greatly decrease the number potential mimetics which must be screened for EPO activity.

The invention may be implemented in hardware or software, or a combination of both. However, preferably, the invention is implemented in computer programs executing on programmable computers each comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program is preferably implemented in a high level procedural or object oriented programming language to communicate with a computer system. However, the programs can be implemented in assembly or machine language, if desired. In any case, the language may be a compiled or interpreted language.

Each such computer program is preferably stored on a storage media or device (e.g., ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

Figure 1:
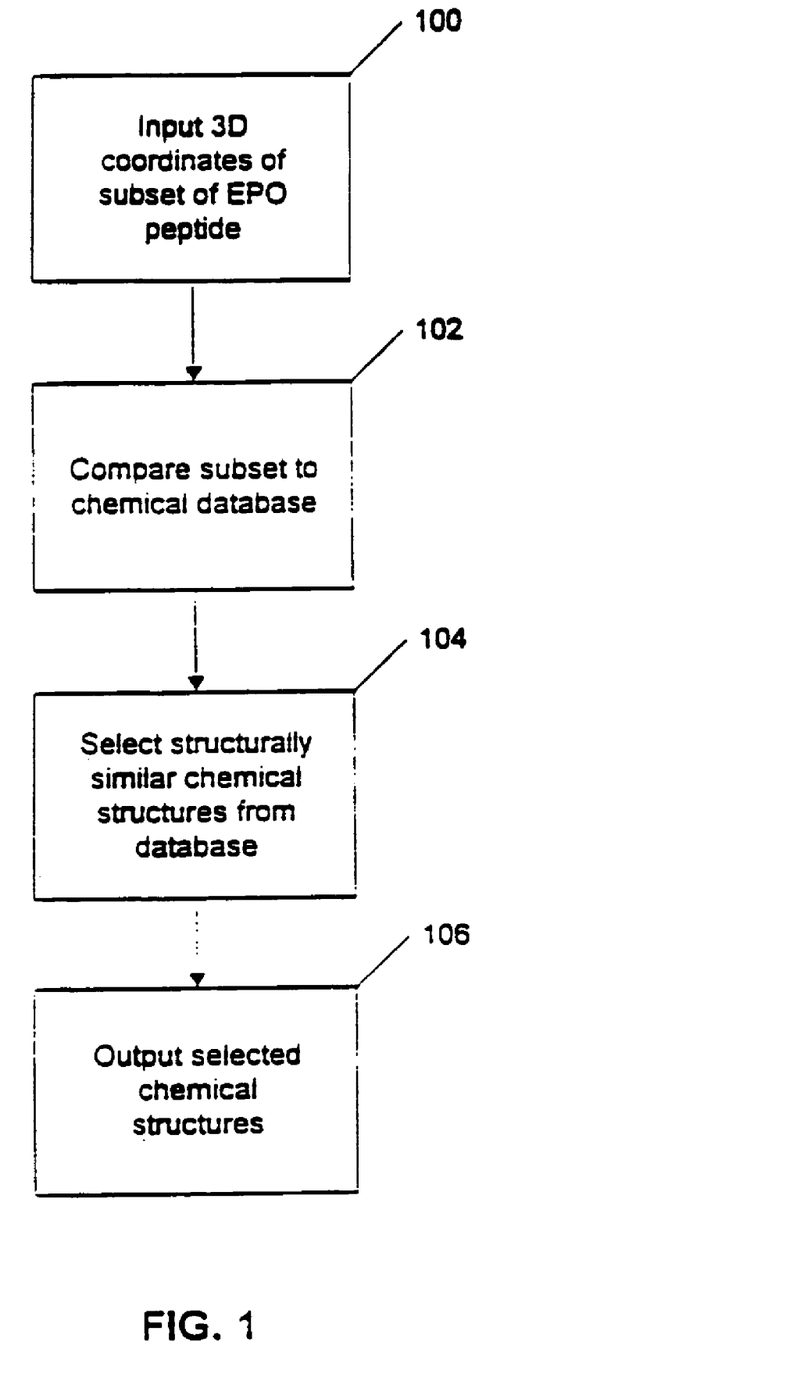
FIG. 1 is a flowchart showing a first method for identifying potential mimetics of erythropoietin using a computer system.

FIG. 1 is a flowchart showing a first method for identifying potential mimetics of erythropoietin using a computer system. The method uses a programmed computer comprising a processor, a data storage system, at least one input device, and at least one output device, and comprises the steps of:

(1) inputting into the programmed computer through an input device data comprising the three-dimensional coordinates of a subset of the atoms in the peptide GGTYSCHF-GPLTWVCKPQGG (SEQ ID NO:1) when the peptide is co-crystallized with a portion of the erythropoietin receptor comprising amino acids 1 to 225 of the receptor, thereby generating a criteria data set (STEP 100);

(2) comparing, using the processor, the criteria data set to a computer database of chemical structures stored in the computer data storage system (STEP 102);

(3) selecting from the database, using a program suitable for searching three-dimensional databases to identify molecules bearing a desired pharmacophore (such as those described above or equivalents), chemical structures having a portion that is structurally similar to the criteria data set (STEP 104);

(4) outputting to an output device the selected chemical structures having a portion similar to the criteria data set (STEP 106).

Figure 2:
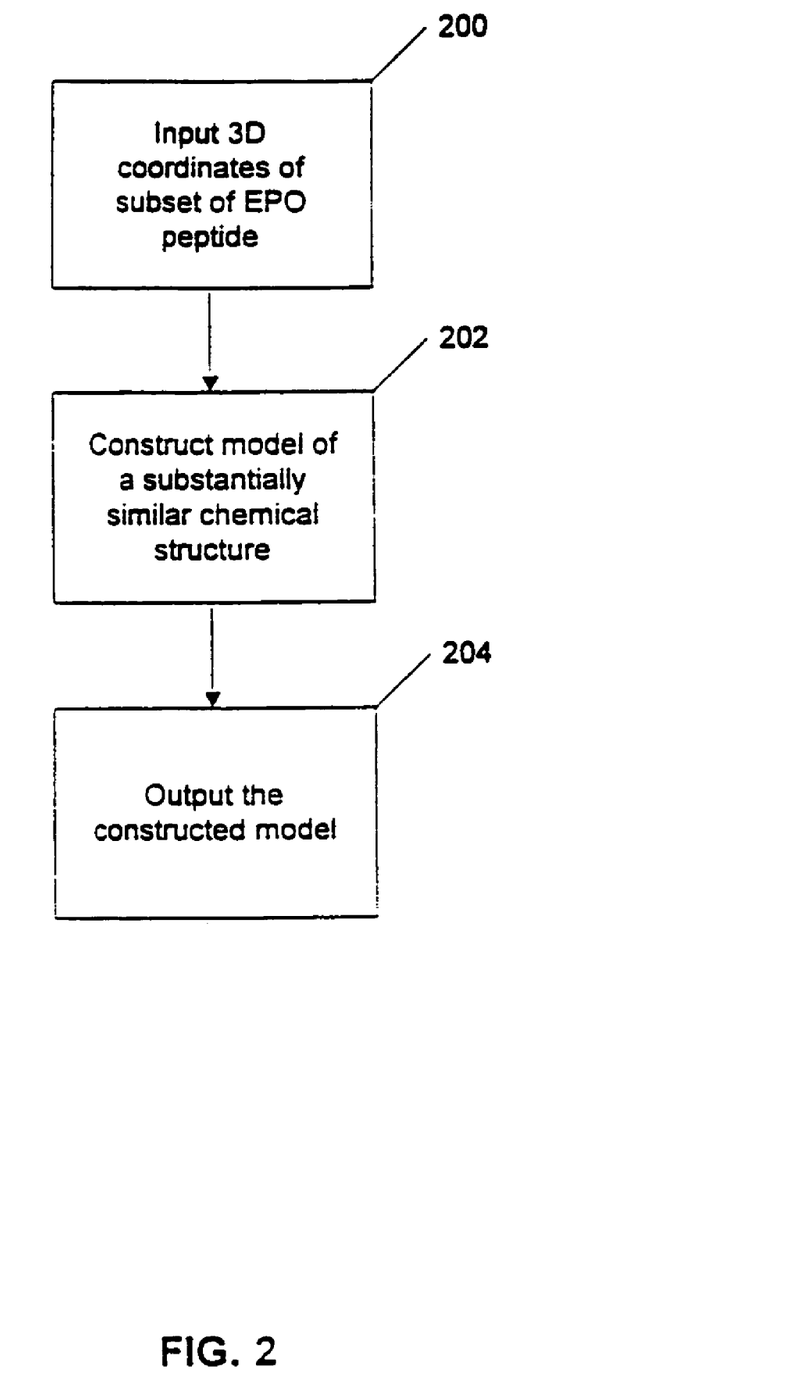
FIG. 2 is a flowchart showing a second method for identifying potential mimetics of erythropoietin using a computer system.

FIG. 2 is a flowchart showing a second method for identifying potential mimetics of erythropoietin using a computer system. The method uses a programmed computer comprising a processor, a data storage system, at least one input device, and at least one output device, and comprises the steps of:

(1) inputting into the programmed computer through an input device data comprising the three-dimensional coordinates of a subset of the atoms in the peptide GGTYSCHF-GPLTWVCKPQGG (SEQ ID NO:1) when the peptide is co-crystallized with a portion of the erythropoietin receptor comprising amino acids 1 to 225 of the receptor, thereby generating a criteria data set (STEP 200);

(2) constructing using a program suitable for generating chemical structure models (such as those described above or equivalents), a model of a chemical structure having a portion that is structurally similar to the criteria data set (STEP 202);

(3) outputting to the output device the constructed model (STEP 204).

Confirmation of Biological Activity

In order to determine whether a molecule identified using the methods of the invention can act as an EPO mimetic, one or more in vitro or in vivo assays of EPO activity should be performed. For example, mimetic molecules should be able to stimulate proliferation of TF-1 cells (Kitamura et al., J. Cell Physiol. 140:323, 1985) or B6Sut cells (Greenberger et al., Proc. Natl. Acad. Sci. USA 80:2931, 1983), but preferably do not stimulate proliferation of cells which do not bear the EPO receptor. Thus, preferred mimetics do not stimulate proliferation of Mo7e cells (Avanzi et al., Br. J. Haematol. 69:359, 1988).

Potential mimetics can also be tested in a murine model of erythropoiesis. In this assay a potential mimetic is administered to normal mice which express endogenous basal levels of EPO. Reticulocytes are counted, preferably by flow cytometry, to determine whether the candidate mimetic increases reticulocyte levels. An increase in reticulocyte levels indicates that the candidate mimetic is stimulating erythropoiesis. Because the mice used in this assay already express EPO, this assay may be relatively insensitive. As an alternative, candidate mimetics can be assayed in the exhypoxic-polycythemic mouse bioassay. In this assay polycythemia is induced by conditioning mice in a hypobaric chamber to reduce endogenous EPO levels. A potential EPO mimetic can be administered to a conditioned mouse. Incorporation of $^{59}$Fe into blood serves as a measure of erythropoiesis. This erythropoiesis can be attributed to the candidate mimetic.

The assays described above are examples of suitable assays. Other assays for EPO activity known to those skilled in the art are also useful.

In order to determine the biological activity of a candidate mimetic it is preferable to measure biological activity at several concentrations of candidate mimetic. The activity at a given concentration of candidate mimetic can be compared to the activity of EPO itself.

Structural Data

The coordinates for amino acids 1 to 225 of the human EPO receptor bound to peptide EMP1 are presented in the attached appendix in standard Brookhaven database format. Also included in this appendix is a list of van der Waals interactions. These coordinates can be used in the design and identification of EPO mimetics according to the methods of the invention.

Structure of EBP-EMP1 Complex

The extracellular fragment of human EPO receptor (EPO binding protein, EBP), consisting of residues 1-225, was expressed in *Escherichia coli* and purified as described (Johnson et al., Protein Express. Purif. 7:104, 1996). Rhomboidal-shaped crystals of an EBP complex with EMP1 were obtained in orthorhombic space group $P2_12_12_1$, with cell parameters a=59.2 Å, b=75.5 Å, c=132.2 Å, with two EBP and two peptide molecules in the asymmetric unit and a $V_M$=2.8 Å$^3$/dalton (Matthews, J. Mol. Biol. 33:491, 1968). The crystal structure was determined by multiple isomorphous replacement (MIR) using two heavy atom derivatives (Table 1). Residues 1-2 and 19-20 of each peptide as well as residues 1-9, 21-23, 164-166, 221-225 of receptor molecule I, and residues 1-9, 21-23, 133-135, 221-225 of receptor molecule II had poor or no electron density and are excluded from the structure analyses An important break in the electron density that affects the structure interpretation occurs for the three residues (Arg$^{21}$-Gly$^{22}$-Pro$^{23}$) that link the amino terminal α-helix to the first β-strand in D1 of both receptor molecules. A molecular packing diagram shows the proximity of a second non-crystallographically related dimer in the crystal that gives two possibilities of how this three-residue linker may be connected. The current choice of linker connectivity is based on a structure of another independent EBP-peptide complex at higher resolution (2.5 Å), which shares a similar molecular packing, but for which the electron density is clear for these three residues. At present there are no experimental data to verify whether this N-terminal α-helix exists in solution or is a crystallization packing artifact. Notably, this helical region is not observed in the published structures of hGHbp (begins at residue 32, deVos et al., Science 255:306, 1992), PRLR (begins at residue 2, without any defined secondary structure until the first β-strand, residue 6; Somers et al., Nature 372:478, 1994), the INF-γRα (begins at residue 17; Walter et al., Nature 376:230, 1995) or the tissue factor (begins at residue 3 without any defined secondary structure until the first β-strand, residue 11; Muller et al., Nature 370:662, 1994).

The EBP monomer folds into two domains, D1 and D2, that form an L-shape with the long axis of each domain aligned at approximately 90° to each other; the overall molecular dimensions are 45 Å×52 Å×62 Å. The N-terminal domain (D1, residues 10-114) and C-terminal domain (D2, residues 119-220) are connected by a short four residue α-helix linker. Both domains are more closely related in overall topology to Fibronectin type-III (FBN-III) domains than to Ig domains (Bork et al., J. Mol. Biol., 242:309, 1994). The FBN-lll fold is composed of two antiparallel β-pleated sheets, consisting of strands A, B, E and strands G, F, C and C', and is found in the two domains of the human growth hormone (de Vos et al., Science 255:306, 1992) and prolactin (Somers et al., Nature 372:478, 1994) receptors, the D1 and D2 domains of the α chain of interferon-γ receptor (IFN-γRα) (Walter et al., Nature 376:230, 1995), the D2 domain of CD4 (Wang et al, Nature 348:411, 1990; Ryu et al., Nature 348:419, 1990), the two domains of tissue factor (Muller et al., Biochemistry 33:10864, 1994; Harlos et al., Nature 370:662, 1994), the third fibronectin-type repeat of tenacin (Leagy et al., Science 258:987, 1992) and the D2 domain of the chaperone protein PapD (Holmgren et al., Nature 342:248, 1989). The FBN-III topology differs from an Ig constant domain by a shift of strand D from one β-sheet (strands A, B, E and D) to the other (strands G, F, C, C'), where it is defined as the C' strand. Superposition of equivalent β-sheet core residues of the D1 and D2 domains in EBP gives an r.m.s. deviation of 2.3 Å for 77 Cα pairs, which is significantly larger than the corresponding domain overlaps for hGHbp (1.1 Å) and PRLR (0.8 Å), and reflects a difference in the subclass of fold between the two EBP domains.

In D1, a short α-helix (residues 10-20), precedes the first β-sandwich that is better described as a hybrid of the FBN-III fold with an Ig fold (residues 24-114), rather than strict FBN-lll topology. In this h-type fold (Wang et al., Nature 348:411, 1990; Ryu et al., Nature 348:419, 1990), the C' strand is long and interacts first with strand C and then switches to interact with strand E (where C' changes its designation to strand D) forming a four-on-four strand β-sandwich. D1 contains the two conserved disulfide bridges linking $Cys^{28}$ (βA) to $Cys^{28}$ (βB) and $Cys^{67}$ (βC') to $Cys^{83}$ (βE). The number of residues between the cysteine pairs that form the two disulfide bridges are 9 and 15 for EBP, compared to 9 and 10 in both GHR and PRLR. The longer connection between strands C' and E enables the second half of strand C' to become strand D. This h-type topology is not found in either of the two s-type GHR domains. A potential glycoylation site exists on residue $Asn^{52}$ which is located towards the end of the loop region connecting the βB and βC stands. Although $Asn^{52}$ is not glycosylated in this bacterially expressed protein, an external cavity around the $Asn^{52}$ side chain could easily accommodate a carbohydrate moiety.

A helical linker (residues 115-118) connects D1 to D2 (The φ, Ψ torsion angles for the interdomain helical linker for $Ile^{115}$, $Asn^{116}$, $Glu^{117}$ and $Val^{118}$ are −50° −27°, −76°, −21°,−99°, 26°, and −151°, 38° respectively.) and has been observed in other members of this receptor family, hGHbp, PRLR, IFN-γRα and tissue factor. In EBP, the domain association is further restricted by a mixed assortment of hydrogen bonding, hydrophobic interactions and one salt bridge (between $Arg^{12\ and\ Asp122}$) from 11 residues of D1 and 12 residues of D2 with a total buried surface [The molecular surface areas buried by interaction were calculated using the program MS (Connolly, J. Appl. Crystallog, 16:439, 1983) using a 1.7 Å probe sphere and standard atomic radii (as described in Davies, et al, Ann. Rev. Biochem. 59:439, 1990). There may be some discrepancies between values reported here and other (deVos et al., Sicnce 255:306, 1992) published values due to use of a different algorithm (Connolly) vs. Lee et al., J. Mol. Biol., 55: 379, 1971) and probe radii. For clarity all values reported here have been calculated in the same way for better comparison between the receptors] of 950 Å$^2$ for the two domains.

D2 (residues 119-220) folds into the standard FBN-lll (s-type) topology with one free cysteine and no disulfide bridges, consistent with GHR and PRLR that have three and two disulfide bridges, respectively, in D1 but none in D2. After the α-helix linker, D2 begins with an irregular coil (residues 118-126) that contains $Pro^{124}$ which is conserved in the structures of hGHbp, PRLR, tissue factor and EFNγ-Rα, and based on sequence alignment, in most class-1 and class-2 cytokine receptors (Bazan, Proc. Natl. Acad. Sci. USA 87:6934, 1990). This short coil ends with $Gly^{124}$ which has a positive φ (φ, Ψ=52°, 40°) consistent with the equivalent $Ala^{136}$ and $Ala^{101}$ torsion angles in hGHbp (φ, Ψ=63°, 68°) and PRLR (φ, Ψ=58°, 38°). The $Pro^{124}$ region forms an analogous extended bulge conformation adjacent and parallel to a corresponding bulge containing the WSXWS motif. The WSAWS sequence forms a modified wide β-bulge (Richardson, Adv. Prot. Chem. 34:167, 1981) and is located in an extended chain region immediately preceding the βG strand that would normally connect to the membrane spanning region of the EPOR.

The quaternary structure of the complex is composed of two peptides and two receptors that form a T-shapes assembly. A noncovalent peptide dimer interacts with two receptor molecules to generate an almost perfect 2-fold symmetrical arrangement. After superposition of D2 of the two EBP molecules in the dimer, the centers of mass of the two D1 domains are only 0.8 Å apart, sufficient to perturb perfect two-fold symmetry. Separate superposition of the corresponding D1 and D2 of each receptor in the dimer results in r.m.s. deviations of 0.53 Å (105 D1 Cα pairs) and 0.47 Å (93 D2 Cα pairs).

The cyclic EMP1 contains a single disulfide bridge between $Cys^{P6}$ and $Cys^{P15}$, which links two short β-strands (residues 4-7 and 13-16) that are connected by a slightly distorted type 1 β-turn [$Pro^{P10}$ (i+1) and $Leu^{P11}$ (i+2) of the β-turn have φ, Ψ=−62°, −38° and −99°, −60°, respectively. The carbonyl oxygen of $Leu^{P11}$ has a hydrogen bond to EBP distorting the Ψ value from its normal 0°±30° (i+2) in a standard type I β-turn.] consisting of residues $Gly^{P9}$-$Pro^{P10}$-$Leu^{P11}$-$Thr^{P12}$. Each peptide has a very close association with its other peptide partner and buries 320 Å of its 1220 Å² molecular surface in this interaction (Connely, J. Appl. Crystallog. 16:439, 1983; Davies et al., Ann. Rev. Biochem. 59:439, 1990; Richards, J. Mol. Biol. 55:379, 1971). Four hydrogen bonds between the mainchains of the two peptides results in formation of a four-stranded anti-parallel β-pleated sheet (Table 2). Two symmetric hyrdophobic cores are assembled by peptide dimerization and are comprised of the disulfide bridges and the side chains of $Tyr^{P4}$, $Phe^{P8}$ and $Trp^{P13}$. The construction of each hydrophobic core resembles a box which places the aromatic rings of $Phe^{P8}$, $Trp^{P13}$ and $Tyr^{P4}$ (from the other peptide) and the disulfide bridge ($Cys^{P6}$-$Cys^{P15}$) at the corners. The two glycine residues at either end of the peptide are not structured.

The peptide dimer is embedded in a deep crevice between two EBP receptor molecules. A portion of each peptide monomer interacts with both receptor molecules. The binding sites of each EBP are practically identical due to the 2-fold symmetric interactions imposed on binding the peptide dimer. The four major contact areas on EBP come from segments on four loop regions (L1, L3, L5, L6) that connect strands A to B (L1 residues 33-34) and F to G (L6 residues-90-94) in D1 and strands B to C (L5 residues 148-153) and F to G (L6 residues 203-205) in D2. The total buried molecular surfaces in the peptide-EBP assembly are 840 Å² and 880 Å² for the two peptides and EBP's, respectively. The peptide-EBP interaction can be separated into distinct hydrophobic (67%) and polar (33%) areas. A hydrophobic core is formed between the peptide and receptor and comprises $Phe^{93}$, $Met^{150}$ and $Phe^{205}$ from one EBP molecule and the peptide hydrophobic box consisting of $Phe^{P8}$ and $Trp^{P13}$ from one peptide and $Tyr^{P4}$ and $Cys^{P15}$ from the other peptide. The polar interactions are located mainly at the bottom of the binding crevice and are mainly with loop L5 in D2. Five of the six hydrogen bonds are between the mainchain of the β-turn residues $Gly^{P9}$, $Pro^{P10}$ and $Leu^{P11}$ from one peptide with the mainchain and sidechain hydroxyl of conserved $Tyr^{P4}$, which crosses over its other peptide partner, to interact with loop L3 (Table 2). The EBP-EBP interaction makes a surprisingly minor contribution to the overall stability of the complex where the inter-receptor buried molecular surface is only 75 Å², contributed by $Leu^{15}$ and $Arg^{178}$ from each receptor molecule.

EMP1 is one of a family of sequences that contain several conserved residues, besides the cysteines (Hansen, Ann. Rev. Microbiol. 47:535, 1993). The most structurally significant of these consensus residues appear to be $Tyr^{P4}$ and $Trp^{P13}$, which along with the disulfide bridge have a major contribution to the hydrophobic core of the peptide-peptide interaction. Moreover, these two aromatic residues play a pivotal role in peptide-receptor interaction and in receptor dimerization.

Dimerization of EBP in Solution

To explore the interaction of EMP1 with EBP in solution we employed a bifunctionalsulphydryl reactive crosslinker DPDPB, [1,4-di-(2'-pyridyldithio propionamido) butane], in an attempt to stabilize a peptide-dependent dimeric structure. The choice of crosslinker was based on previous experiments with amine-reactive crosslinkers that were found to inactivate EBP. EBP contains a single free sulphydryl ($Cys^{181}$) in D2 which is potentially reactive to crosslinking reagents (The DPDPB crosslinker itself does not inactivate the EPO binding potential of EBP nor the proliferative properties of EMP1). A dimeric EBP product is formed by co-incubation of EMP1, DPDPB and EBP. The amount of dimeric product increases with peptide concentration and no significant dimer product is observed in the absence of peptide. DPDPB-crosslinked products formed through disulfide-exchange reactions should be readily reversible by reduction as is seen for the covalently-linked EMP1-mediated dimer. Furthermore, we have constructed a covalently-linked dimeric form of EMP1 that demonstrates increased biological potency (Johnson et al, in preparation). The $Cys^{181}$ residues in D2 of the EBP dimer are 20.7 Å apart (Sγ-Sγ distance) which approximates the 16 Å length (and approximately 2 Å in bond length at each end) of the DPDPB cross-linker. Thus EMP1 mediates formation of a soluble EBP dimer complex in solution consistent with the crystal structure.

The WSXWS Motif (SEQ ID NO:2)

The WSAWS sequence (SEQ ID NO:3) (residues 209-213) corresponding to the WSXWS box (SEQ ID NO:3) occurs in a .beta.-bulge (Richardson, Adv. Prot. Chem. 34:167, 1981; Chan et al, Protein Science, 2:1574, 1993) immediately preceding .beta.-strand G in D2. Residues in this motif do not interact with ligand, have no role in receptor-receptor interactions and are located on the opposite side of the receptor-receptor and receptor-ligand interface. The WSAWS box represents only a segment of a complex array of interactions that involves several other conserved side chains from the four-stranded .beta.-sheet in D2. The indole ring systems of Trp.sup.209 and Trp.sup.212 point toward an external concave surface of the .beta.-sheet and are only partially solvent exposed, whereas the Ala-.sup.211 side chain points directly out into solution. The amides and hydroxyls of both Ser.sup.210 and Ser.sup.213 form hydrogen bonds with the main chain of residues 198 and 196 of adjacent strand F in a pseudo .beta.-sheet type interaction that resembles a modified wide .beta.-bulge (Richardson, Adv. Prot. Chem. 34:167, 1981; Chan et al., Protein Science, 2:1574, 1993) where the sidechain hydroxyl rather than the carbonyl oxygen makes the .beta.-sheet interaction. The .beta.-bulge architecture places the two Trp residues, which are spread four residues apart, on the same side of the .beta.-sheet and not on opposite sides as in normal .beta.-sheet or extended chain structures. The guanidinum group of Arg.sup.197 from Strand F, the central residue (Richardson, Adv. Prot. Chem. 34: 167, 1981; Chan et al., Protein Science, 2:1574, 1993) in the bulge, is positioned exactly between the two Trp indole rings to form an extended .pi.-cation system (Kumpf et al., Science 261: 1708, 1993. The center of the pyrrole ring of Trp.sup.209, the N.epsilon. of the Arg.sup.197 and the center of the benzene ring of Trp.sup.212 are positioned on a straight line with the three planes of the conjugated systems stacked parallel to each other at a approximately 4 .ANG. spacing. In addition, the aliphatic portion of the Arg.sup. 199 side chain has hydrophobic interactions with the indole ring of Trp.sup.209, completing the alternating stacking of two aromatic and two positively-charged amino acid residues. The side chain of Glu.sup.157 forms a hydrogen bond with Arg.sup.197 presumably to help orient the guanidinium group and add some specificity and stabilization to the system.

It appears then that the linear WSXWS motif (SEQ ID NO:2) identified from sequence alignments of cytokine receptors represents only a component of a more complex conformational unit that contributes a significant structural feature to D2. Aromatic residues have previously been suggested to have a stabilizing effect and play a role as a folding nuclei in structures of antiparallel .beta.-sandwiches (Finkelstein et al., Protein Eng. 6:367, 1993). The amino-aromatic parallel stacking between the guanidinium group of arginine, and the aromatic rings is a common feature in protein structures (Burley et al., Adv. Prot. Chem., 39:125, 1988; Flocco et al., J. Mol. Biol., 235:709, 1994), but a parallel triple stacking of .pi.-cation systems is rare (Kim et al, Biochemistry 32:8465, 1993) although observed in other class-1 cytokine receptors, hGHbp and PRLR.

The structural equivalents of the WSXWS motif (SEQ ID NO:2) in hGHbp (YGEFS (SEQ ID NO:4)) and PRLR (WSAWS (SEQ ID NO:3)) are involved in an even more intricate and complex array of .pi.-cation interactions. The .pi.-cation system is extended in hGHbp and PRLR to include an additional aromatic residue (Trp.sup. 186 for hGHbp and Trp.sup.156 for PRLR) from the loop region that links .beta.C and .beta.C' in D2 and a positively-charged residue (Arg.sup.211 for hGHbp and Arg.sup.147 for PRLR) that stacks between the Trp and the second aromatic residue. The additional Arg residue is contributed either from the .beta.F strand as in hGHbp (Arg.sup.211) or from .beta.C as in PRLR (Arg.sup.147); the glutamine residue that hydrogen bonds and orients the arginine also switches strands. Sequence alignments suggest that this Arg-Gln switch could be common to other members of the class-1 cytokine receptor family. The extended .pi.-cation system in hGHbp and PRLR consists of five positively charged and three aromatic residues stacked in an alternating order which comprises of Lys.sup.215, Tyr.sup.222, Arg.sup.213, Phe.sup.225, Arg.sup.211, Trp.sup.186, Lys.sup.179 for hGHbp and Lys.sup.185, Trp.sup.191, Arg.sup.183, Trp.sup.194, Arg.sup. 147, Trp.sup.156, Lys.sup.149 for PRLR. The first aromatic-Arg-aromatic trio are approximately 4 .ANG. apart, as in EBP, but the second system is stacked closer together at approximately 3.6 .ANG. spacings consistent with .pi.-.pi. interaction (Burley et al., Adv. Prot. Chem., 39:125, 1988; Flocco et al., J. Mol. Biol., 235:709, 1994). The outer lysines also use the aliphatic portions of their side chains to form hydrophobic interactions with the aromatic rings. Based on sequence alignments with other members of the class-1 cytokine receptor superfamily, such structurally extended .pi.-cation systems could exist in human thrombopietin, IL-6 and ciliary neurotrophic factor receptors, and in human IL-4 receptor based on structural modeling (Gustchina et al., Proteins 21:140, 1995). Although IFN-.gamma.R.alpha. and tissue factor do not have a WSXWS motif (SEQ ID NO:2), the corresponding sequences TTEKS (SEQ ID NO:5) (residues 213-217) for IFN-.gamma.R.alpha. (Walter et al., Nature 376:230, 1995) and KSTDS (SEQ ID NO:6) (residues 201-205) for tissue factor (Muller et al, Biochemistry 33:10864, 1994; Harlos et al., Nature 370:662, 1994), maintain a very similar .beta.-bulge. The consensus sequence among these five x-ray structures indicates that a serine or threonine in positions 2 and 5 maintain a common set of hydrogen bonds between their side chain hydroxyls and the mainchain of the neighboring strand. Only in hGHbp is there no hydroxyl-containing residue in position 2, but Ser.sup.226 still maintains the equivalent interaction. A Ser.sup.226 to Ala mutation abrogates hGHR binding to hGH, and its expression on the cell surface is drastically reduced (Baumgartner et al., J. Biol. Chem., 269:29094, 1994). In GM-CSFR.alpha. and IL-2R.beta., point mutations of the serine residues cause a substantial decrease in cell surface expression but little or no effect on ligand binding (Ronco et al., J. Biol. Chem. 269:277, 1994; Miyazai: et al., EMBO Journal 10:3191, 1991).

Conservation of the WSXWS motif (SEQ ID NO:2) in EPOR or its equivalent in other members of the class 1 cytokine receptors has been proposed to be essential for biological activity and was thus assumed to be part of the receptor binding site (Yoshimura at al., J. Biol. Chem. 267:11619, 1992; Quelle, Mol. Cell. Biol. 12:4553 1992). For EPOR, a systematic study of 100 mutations of the WSAWS sequence (SEQ ID NO:3) demonstrates that most of the mutations of the two tryptophan and serine resulted in molecules that did not reach the cell surface but were retained in the endoplasmatic reticulum (Hilton et al., Proc. Natl. Acad. Sci. USA 92:190, 1995; Hilton et al., J. Biol. Chem. 271:4699, 1996). Furthermore, an Ala.sup.211 to Glu mutation in the WSAWS sequence (SEQ ID NO:3) resulted in better transportation from the ER to the Golgi and a 3-5 fold increase of the number of EPOR molecules on the cell surface compared to the wild-type (Hilton et al., Proc. Natl. Acad. Sci. USA 92:190, 1995; Hilton et al., J. Biol. Chem. 271:4699, 1996). These results support our conclusion that the WSXWS sequence (SEQ ID NO:2) plays an important role in the structure and folding of D2 in EPOR and other related receptors.

Comparison with Other Cytokine-receptor Complex Structures

The overall quaternary structure of the peptide-EBP complex substantially from the equivalent arrangement in the hGH-hGHR complex. The non-symmetric nature of the single four-helix-bundle structure of the growth hormone ligand results in an asymmetric homo-dimerization of the receptor that corresponds to a 159° rotation between receptors compared to the almost perfect 2-fold (180°) rotation for the EBP-peptide complex. The tertiary arrangement of domains within EBP and hGHbp is also somewhat different. When the equivalent EBP and hGHbp D2 domains are superimposed on each other, their corresponding D1 domains differ by a 12° rotation and a 4.3 Å translation.

The mechanism of hGH binding to its receptor has been well studied (Wells, Curr. Opin. Cell Biol. 6:163, 1994; Clackson et al., Science 267:383, 1995) and is sequential. Initial high affinity (nM) binding of the hormone with one receptor results is a buried surface of 1130 Å$^2$ on the receptor. The second hGHbp2 has a substantially smaller interface (deVos et al., Science 255:306, 1992) with the second binding site on hGH and interacts only with the preformed 1:1 complex to generate buried surface areas of 740 Å$^2$ with hGH and 440 Å$^2$ with the first hGHbp1 (deVos et al., Science 255:306, 1992; (Wells, Curr. Opin. Cell Biol. 6:163, 1994; Clackson et al., Science 267:383, 1995). The binding determinants of each hGHbp are comprised of the six recognition loops (L1-L6), three of which (L1-L3) come from one end of the β-sandwich structure in D1, one from the interdomain linker and two from D2.

Although these two receptor complexes, EBP-EMP1 and hGH-hGHbp, have different dimeric arrangements, which probably in this case represent differences in the size and shape of the natural versus synthetic ligand, both receptors share equivalent ligand recognition loops, L1, L3, L5 and L6 for the EBP and L1 to L6 for the hGHbp. A non-active PRLR, complexed with only one molecule of hGH, also uses the same contact loops (L1 to L6) (Somers et al., Nature 372:478, 1994). Based on similarity of the ligand recognition sites in hGHbp and PRLR, one would expect that the binding site of EBP, when its natural EPO ligand is bound, would extend to include two additional loops, L2 and L4, that comprise residues 59-63 (2) between strands C to C', and residues 110-118 (L4) from the carboxyl end of βG in D1 and the interdomain linker. These six loops in EBP, hGHbp and PRLR area in structurally equivalent positions but vary in size, amino acid composition and conformation although the interacting portions of each loop (side or tip)

remain similar, L1, L2, L3, L5 interact mainly with their tips and L6 with its side. In EBP, the L5 loop is three residues shorter than in hGHbp and PRLR, where the L6 loop is three and four residues longer than in hGHbp and PRLR, respectively. The L2 loop also varies (6 to 10 residues) among the three receptors but in EBP does not participate in peptide binding, and in hGHbp is partially disordered, although it does contact the hormone. In one respect, this situation is similar to the complementarity-determining regions (CDR's) in antibodies, where changes in length and sequence of the six binding loops impose specificity for different antigens, whereas the framework itself remains constant (Wilson et al., Ciba Foundation Symposium. Wiley, Chichester, 1991, Vol. 159, p. 13).

It has been shown for the hGH-hGHbp complex that only a subset of 9 out of 33 interacting residues that make up the structural epitope of the receptor constitute a functional epitope or hot spot (Wells, Curr. Opin Cell Biol. 6:163, 1994; Clackson et al., Science 267:383, 1995) where high affinity binding interaction takes place. This reduced epitope is substantially smaller than the structural epitope and is comprised from residues ($Arg^{43}$, $Glu^{44}$, $Ile^{103}$, $Trp^{104}$, $Ile^{105}$, $Pro^{106}$, $Asp^{165}$, and $Trp^{169}$) which are located in contact loops L1, L3 and L5 with the most significant contribution (>4.5 kcal/mol) coming from two aromatic residues ($Trp^{104}$ and $Trp^{169}$) in L3 and L5 (Wells, Curr. Opin. Cell Biol. 6:163, 1994; Clackson et al., Science 267:383, 1995; Wells, Proc. Natl. Acad. Sci. USA 93:1, 1996). In EBP, $Phe^{93}$ is equivalent to $Trp^{104}$ in hGHbp, as suggested previously (Wells, Curr. Opin. Cell Biol. 6:163, 1994; Clackson et al., Science 267:383, 1995; Wells, Proc. Natl Acad. Sci. USA 93:1, 1996; Jolliffe et al., Nephrol. Dial. Trans. 10:suppl. 2, 28, 1995), but there is no homologous residue to $Trp^{169}$ in the shorter L5 loop. In the EBP-EMP1 complex, the $Phe^{P8}$ peptide aromatic side chain occupies the equivalent position of the $Trp^{169}$ side chain in hGHbp. One can assume that when EPO binds to its receptor, the hormone may provide an aromatic residue to the hydrophobic core of the binding interface and/or the L6 loop in EBP may play a more significant role in the hormone binding than in hGHbp, since it is 3 residues longer and contains the aromatic $Phe^{205}$.

In these three class-1 receptor structures, some loops are disordered which are in D2 for EBP for EBP (residues 164-166 in EBP1 and 1333-135 in EBP2) and in D1 for both hGHbp (residues 55-58, 73-78 for hGHbp 1 and 54-60, 73-75 for hGHbp2) and PRLR (residues 31-33, 84-86). Otherwise, these three class-1 cytokine receptors do not differ greatly in their over all tertiary structures; D1 and D2 have broadly similar general arrangement in all three receptors such that the angle between the long axes of the two domains is approximately 90 degrees. It is this arrangement of domains that allow these particular L1-L6 loops to be available for the recognition and binding of ligands. In a 2:2 complex between IFN-γ and its class-2 receptor IFN-γRα, D1 and D2 are related by a 125 degree angle, which elongates the receptor and restricts the binding determinants that can be used for interaction with hormone; the L1 loop now becomes buried in the D1-D2 interface, although the other five loops (L2-L6) are still available for ligand interaction. This elongated interdomain arrangement is also observed in tissue factor (Muller et al., Biochemistry 33:10864, 1994; Harlos et al., Nature 370:662, 1994) which has a distant relationship to the cytokine receptor superfamily.

A mutational analysis of the EBP molecule indicates that the most crucial amino acid residue for binding EPO is $Phe^{93}$ in the L3 loop (Jolliffe et al., Nephrol. Dial. Trans. 10:suppl 2, 28, 1995). The Phe93Ala mutant shows an increase int he $IC_{50}$ compared to is the wild-type by a factor of approximately 1000, whereas other mutants (Ser91Ala, Ser92Ala, Val94Ala, Met150Ala and His153Ala) show small relative increases in the $IC_{50}$ of only 2.5-12.5 fold). The side chain of $Phe^{93}$ buries 66 $Å^2$ of molecular surface, which is the highest among interacting side chains. In hGHbp, the corresponding Trp104Ala mutation results in an increase in the $K_d$ by a factor of more than 2,500 compared to the wild-type indicating the equivalent importance of this residue in hGH binding and its key contribution to the hydrophobic core of the functional epitope (Wells, Curr. Opin. Cell Biol. 6:163, 1994; Clackson et al., Science 267:383, 1995; Bass et al. Proc. Natl. Acad. Sci. USA 88:4498, 1991).

The Role of Dimerization on Signal Transduction

In the EBP-EMP1 complex structure, we surprisingly observe that a peptide, unrelated in sequence and probably in structure, to the natural ligand, can induce a biologically active dimerization of EPO receptor that promotes signal transduction and cell proliferation Comparison of three class-1 cytokine receptor complexes, whose structures have been determined so far, suggests that when the natural EPO hormone, which is proposed to have a structure of a four-helix bundle (Boissel et al., J. Biol. Chem. 268:15983, 1993), induces receptor dimerization, it is more likely to resemble the hGH-hGHbp assemblage. This would suggest that more than one mode of productive extracellular dimerization is permissive for intracellular dimerization of the cytoplasmic domains with two JAK2 molecules in order to initialize the cascade of events that produces the biologically relevant signal (Ihle et al., Seminars in Immunology 5:375, 1993; Klingmuller et al., Cell 80:729, 1995). The peptide-EBP structure would then represent only one possible dimeric arrangement that promotes signal transduction.

Mutant EPOR molecules, containing a single Arg to Cys mutation ($Arg^{130}$ in human and $Arg^{129}$ in murine), have been shown to form biologically active dimers in the absence of EPO (Yoshimura et al., J. Biol. Chem. 267:11619, 1992); Watowich et al., Proc. Natl. Acad. Sci. USA 89:2140, 1992; Watowich et al., Mol. Cell. Biol. 14:3535, 1994), suggesting that extracellular recptor homo-dimerization may be sufficient in itself for signal transduction. It has been shown in another system (Spencer et al., Science 262:1019, 1993) that activation of a specific set of transcription factors can be induced by the chemical crosslinking of cytoplasmic domains of modified cell membrane receptors that do not contain the extracellular and transmembrane domains. These receptors are not related to the cytokine receptor superfamily but illustrate that oligomerication plays a key role in activation of the receptor, and that the main functional role of the extracellular, ligand-binding domain is to allow (in the presence of ligand) dimerization or oligomerization and induce similar association of the cytoplasmic domains.

Mutageneses experiments originally suggested a role for the WSXWS motif (SEQ ID NO:2) in this cell signalling process (Yoshimura et al, J. Biol. Chem. 267:11619, 1992; Queue et al. Mol. Cell. Biol. 12:4553, 1992; Chiba et al., Biochem. Biophys. Res. Comm. 184:485, 1992) possibly by promoting receptor homo-dimerization. However, truncation mutants of EPOR (Mura et al., Arch. Biochem. Biophys. 306:200, 1993) do not confirm this role for the WSXWS motif (SEQ ID NO:2). The EBP-EMP1 complex structure shows that the WSXWS motif (SEQ ID NO:2) of the EPOR, as for the hGH-hGHbp complex (deVos et al, Science 255:306, 1992) is located on the opposite face of the molecule from the receptor dimerization. In the absence of unliganded structures for the extracellular domains of EPOR, hGHR and PRLR, it is not possible to determine whether any conformation change occurs on ligand binding that would involve the WSXWS box (SEQ ID NO:2). Apart from being a striking structural feature in D2, and its obvious proximity to the membrane spanning domain, one cannot rule out possible interactions of this region with some other cell surface molecules that are involved somehow in the signal transduction process.

Towards Design of Small Molecule Mimetics

The structure of the EMP1 dimer demonstrates that a peptide considerably smaller than the natural hormone can act as an agonist and induce the appropriate biological response. The peptide can be assumed to form a substantially smaller contact interface than the natural hormone with the receptor. The peptide binding site in EBP forms an almost flat surface, which is mainly hydrophobic in nature, without any cavities or charged residues that are normally essential for the specific targeting of small molecule ligands to a receptor binding site. The hGHbp study (Wells et al., Science 267:383, 1995; Wells, Proc. Natl. Acad. Sci. USA 93:1, 1996) shows that only a small part of the observed structural binding site, the so-called functional epitope (supra), contributes most of the binding energy and strongly implied that a "minimized" hormone designed to interact with this site could form sufficient interactions to activate the receptor. Furthermore, the limited site of interaction of the small agonist peptide with the EBP corresponds almost exactly to the smaller functional epitope derived from alanine scanning of hGH and hGHbp. Thus, by a different approach, we have arrived at the similar conclusion that a small number of key interactions can contribute to a functional epitope on a receptor. Understanding of this simplified interaction surface can be now combined with further mutational studies to assist in identifying the most crucial residues in the functional epitope, and consequently provide a more practical target for drug design.

Data Collection. MIR and Refinement Statistics

The crystallographic data is summarized in Table 1. Native crystallographic data were collected on a Siemens multiwire area detector mounted on an Elliott GX-18 generator, operating at 40 kV and 55 mA, with a crystal-to-detector distance of 120 mm. Two derivative data sets were collected on a MAR image plate mounted on a Siemens generator operating at 50 kV and 80 mA, with crystal-to-image plate distance of 150 mm. Data were integrated, scaled and reduced using the programs XENGEN (Howard et al., J. App. Cryst. 20:383, 1987) for the native data and DENZO/SCALEPACK (Otwinowski et al., SERC Darsbury Laboratory, Warrington, 1993) for the derivative data. Initial multiple isomorphous replacement anomalous scattering (MIRAS) phases were calculated to 3.1 Å using the program package PHASES (Furey, American Crystallographic Association Fortieth Anniversary Meeting, New Orleans, La., 1990) with a mean figure of merit of 0.64 (25.0-3.1 Å). Phases were refined in PHASES using the solvent flattening protocol to a mean figure of merit of 0.92 (25.0-3.1 Å). The quality of the map was generally good and most of the complex structure (94%) could be fitted using the graphics program O (Jone et al., Acta Crystallogr A47:110, 1991). The register of the amino acid residues was verified from the positions of the two disulfide bridges in D1, and the positions of the two Hg's from the mercury acetate derivative that were correctly assumed to bind to the free $Cys^{181}$ residue. the peptide interpretation was verified from another data set from a complex between EBP and an iodinated peptide ($Tyr^{P4}$ was substituted for p-iodo-Phe), which diffracted to 3.3 Å resolution, that in difference Fourier ($F_{iodo} - F_{phe})\alpha_{MIRAS}$ gave a clear indication of the location of the iodine atoms. The structure was refined using the slow-cooling protocol in X-PLOR 3.1 (Brunger et al., Acta Crystallogr A46:585, 1990; Brunger, X-PLOR, Version 3.1: A System for X-ray and NMR, Yale Univ. Press, New Haven, Conn., 1992) and rebuilt using Fo-Fc, 3Fo-2Fc and SIGMAA (Read, Acta Crystallogr. A42:140, 1986) weighted electron density maps. After every two cycles of refinement, a set of simulated annealing omit maps (7-10%) to reduce model bias was calculated and the entire structure rebuilt. After several cycles of refinement, individual temperature factors were calculated and after 10 cycles of refinement and model building, the R-value was 0.21 for 8.0-2.8 Å data with $F>1\sigma$ (13,984 reflections). The average thermal parameters for receptor I, receptor II and the peptides are 10.5 Å$^2$, 12.3 Å and 10.7 Å respectively. Only one non-glycine residue [$Asn^{164}$ in EBP2], located in a loop region in D1, is in a disallowed region in the Ramachandran plot. No solvent molecules were included in the model due to the moderate resolution (2.8 Å) of the structure determination Binding Contacts Binding contacts are summarized, in part, in Table 2: Hydrogen bond interactions in the binding site of the EBP-EMP1 complex. Due to the symmetrical nature of the complex, peptide-1 and peptide-2 have equivalent interactions with the two EBP molecules. The hydrogen bond interactions were analyzed using HBPLUS (McDonald et al., J. Mol. Biol. 238:777, 1994), based upon both distance (3.9 Å cutoff) and geometrical considerations.

A number of embodiments of the present invention have been described. Nevertheless, it will be understood that various modifications may be made without departing from the spirit and scope of the invention. Accordingly, it is to be understood that the invention is not to be limited by the specific illustrated embodiment, but only by the scope of the is appended claims.

What is claimed is:

1. A computer-assisted method for identifying potential mimetics of erythropoietin, using a programmed computer comprising a processor, a data storage system, an input device, and an output device, comprising the steps of:

(a) inputting into the programmed computer through said input device data comprising the three-dimensional coordinates of a subset of the atoms in the peptide GGTYSCHFGPLTWVCKPQGG (SEQ ID NO:1) when said peptide is co-crystallized with a portion of the erythropoietin receptor comprising amino acids 1 to 225 of said receptor, thereby generating a criteria data set;

(b) comparing, using said processor, said criteria data set to a computer database of chemical structures stored in said computer data storage system;

(c) selecting from said database, using computer methods, chemical structures having a portion that is structurally similar to said criteria data set;

(d) outputting to said output device the selected chemical structures having a portion similar to said criteria data set;

(e) providing a compound having a selected chemical structure; and (f) testing the compound in a biological assay to determine whether it stimulates erythrpoiesis.

2. A computer-assisted method for identifying potential mimetics of erythropoietin, using a programmed computer comprising a processor, a data storage system, an input device, and an output device, comprising the steps of:

(a) inputting into the programmed computer through said input device data comprising the three-dimensional coordinates of a subset of the atoms in the peptide GGTYSCHFGPLTWVCKPQGG (SEO ID NO:1) when said peptide is co-crystallized with a portion of the erythropoietin receptor comprising amino acids 1 to 225 of said receptor, thereby generating a criteria data set;

(b) constructing, using computer methods, a model of a chemical structure having a portion that is structurally similar to said criteria data set;

(c) outputting to said output device the constructed model;

(e) providing a compound having the chemical structure constructed in step (b)); and (f) testing the compound in a biological assay to determine whether it stimulates erythrpoiesis.

* * * * *

UNITED STATES PATENT AND TRADEMARK OFFICE
CERTIFICATE OF CORRECTION

PATENT NO.        : 7,272,508 B2
APPLICATION NO.   : 11/252390
DATED             : September 18, 2007
INVENTOR(S)       : Ian A. Wilson et al.

It is certified that error appears in the above-identified patent and that said Letters Patent is hereby corrected as shown below:

Col. 1, under Government Support, line 19, replace "GM 49491" with --GM 49497--.

Signed and Sealed this

Twenty-seventh Day of November, 2007

JON W. DUDAS
*Director of the United States Patent and Trademark Office*

SEQUENCE LISTING

<160> NUMBER OF SEQ ID NOS: 6

<210> SEQ ID NO 1
<211> LENGTH: 20
<212> TYPE: PRT
<213> ORGANISM: Artificial Sequence
<220> FEATURE:
<223> OTHER INFORMATION: Synthetically generated peptide -continued

```
<400> SEQUENCE: 1

Gly Gly Thr Tyr Ser Cys His Phe Gly Pro Leu Thr Trp Val Cys Lys
1               5                   10                  15

Pro Gln Gly Gly
            20

<210> SEQ ID NO 2
<211> LENGTH: 5
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 3
<223> OTHER INFORMATION: Xaa = any amino acid.

<400> SEQUENCE: 2

Trp Ser Xaa Trp Ser
1               5

<210> SEQ ID NO 3
<211> LENGTH: 5
<212> TYPE: PRT
<213> ORGANISM: Homo sapiens

<400> SEQUENCE: 3

Trp Ser Ala Trp Ser
1               5

<210> SEQ ID NO 4
<211> LENGTH: 5
<212> TYPE: PRT
<213> ORGANISM: Homo sapiens

<400> SEQUENCE: 4

Tyr Gly Glu Phe Ser
1               5

<210> SEQ ID NO 5
<211> LENGTH: 5
<212> TYPE: PRT
<213> ORGANISM: Homo sapiens

<400> SEQUENCE: 5

Thr Thr Glu Lys Ser
1               5

<210> SEQ ID NO 6
<211> LENGTH: 5
<212> TYPE: PRT
<213> ORGANISM: Homo sapiens

<400> SEQUENCE: 6

Lys Ser Thr Asp Ser
1               5
```